United States Patent
Hsu et al.

(10) Patent No.: US 8,728,407 B2
(45) Date of Patent: May 20, 2014

(54) HOLDING DEVICE

(75) Inventors: Ming-Chang Hsu, Hsinchu (TW);
Ming-Hsin Chuang, New Taipei (TW);
Mon-Wen Yang, Hsinchu (TW);
Thomas Y. S. Shen, Hsinchu (TW)

(73) Assignee: Apex Biotechnology Corp., Hsinchu (TW)

( * ) Notice: Subject to any disclaimer, the term of this patent is extended or adjusted under 35 U.S.C. 154(b) by 0 days.

(21) Appl. No.: 13/620,728

(22) Filed: Sep. 15, 2012

(65) Prior Publication Data

US 2013/0121875 A1    May 16, 2013

(30) Foreign Application Priority Data

Nov. 16, 2011 (TW) .............................. 100221643 U

(51) Int. Cl.
*G01N 33/00* (2006.01)
(52) U.S. Cl.
USPC ........ 422/402; 422/400; 422/68.1; 422/82.05
(58) Field of Classification Search
USPC .............................. 422/402, 400, 68.1, 82.05
See application file for complete search history.

(56) References Cited

U.S. PATENT DOCUMENTS

| | | | |
|---|---|---|---|
| 7,585,461 B2 | 9/2009 | Shimp et al. | |
| 7,819,283 B2 | 10/2010 | Chambers et al. | |
| 8,052,943 B2 | 11/2011 | Amano et al. | |
| 2008/0124243 A1 | 5/2008 | Chen et al. | |
| 2009/0108013 A1* | 4/2009 | Van Der Velde et al. | ......... 221/1 |
| 2010/0319170 A1 | 12/2010 | Hsu et al. | |
| 2012/0116706 A1 | 5/2012 | Nakanishi et al. | |
| 2012/0126082 A1 | 5/2012 | Hsu et al. | |

FOREIGN PATENT DOCUMENTS

| | | |
|---|---|---|
| JP | 2003042994 | 2/2003 |
| JP | 2008289805 | 12/2008 |
| JP | 2010078409 | 4/2010 |
| TW | I274158 | 2/2007 |
| TW | M420307 | 1/2012 |
| TW | M422956 | 2/2012 |

\* cited by examiner

*Primary Examiner* — Sam P Siefke
(74) *Attorney, Agent, or Firm* — Jianq Chyun IP Office

(57) ABSTRACT

A holding device disposed in a bio-detecting instrument for holding a test strip is provided, wherein the holding device comprises a first casing, a second casing, an ejecting member, and an elastic member. The second casing is assembled with the first casing to form an accommodating space, wherein the sensing terminals are extended into the accommodating space. The ejecting member comprises a push rod configured to be reciprocated in the accommodating space. The elastic member is configured to be compressed by driving the ejecting member to an ejecting position, where the push rod enters the accommodating space and is adapted to push the test strip outward without being contact with the sensing terminals, and the elastic member is configured to be released by drawing the push rod back from the accommodating space to an initial position.

8 Claims, 5 Drawing Sheets

US 8,728,407 B2

HOLDING DEVICE

CROSS-REFERENCE TO RELATED APPLICATION

This application claims the priority benefit of Taiwan application serial no. 100221643, filed on Nov. 16, 2011. The entirety of the above-mentioned patent application is hereby incorporated by reference herein and made a part of this specification.

BACKGROUND OF THE INVENTION

1. Field of the Invention

The present application is related to a holding device, and more particularly, to a holding device disposed in a bio-detecting instrument for holding a test strip.

2. Description of Related Art

As the global population ages, the number of patients, especially those with metabolic diseases, is growing rapidly and estimated to over 1.1 billions in 2012. Therefore, more medical institutions are required, and handheld Point-of-Care Testing (POCT) systems are developed, as the Preventive Medicine rises.

With respect to handheld Point-of-Care Testing (POCT) systems, the low-invasion biochemical testing system is more preferred than other testing system, due to small required amount of blood. However, although the required amount of sample is reduced, as the volume and size of test strip become smaller, a quantity of blood sample may still remain on the test strip after testing, which brings the risk of infection to whom remove the test strip by hand.

In addition, the recent testing systems are provided with multiple testing terminals, so as to improve testing precision and accuracy, and achieve Multi-function identification. However, the sensing terminals may be impacted or pressed by ejecting mechanisms as rejecting the test strip after the test is completed. After a long period of operation, the sensing terminals may deform and affect the test results.

SUMMARY OF THE INVENTION

Accordingly, the present invention is directed to a holding device disposed in a bio-detecting instrument for holding a test strip, wherein users can remove a test strip from the holding device without drawing the test strip by hand, to eliminate the risk of infection. In addition, sensing terminals of the bio-detecting instrument are not pressed or impacted by the holding device when removing the test strip.

According to an embodiment of the present application, the holding device comprises a first casing, a second casing, an ejecting member, and an elastic member. The second casing is assembled with the first casing to form an accommodating space there between, wherein the sensing terminals are extended into the accommodating space, and the test strip is configured to be delivered into the accommodating space through a first opening and contact with the sensing terminals. The ejecting member comprises a push rod and a first stopper, wherein the push rod is configured to be reciprocated in the accommodating space through the second opening. The elastic member is disposed between the second casing and the first stopper, wherein the elastic member is configured to be compressed by driving the ejecting member to an ejecting position, where the push rod enters the accommodating space and is adapted to push the test strip outward without being contact with the sensing terminals, and the elastic member is configured to be released by drawing the push rod back from the accommodating space to an initial position.

As to the above, the holding device of the present application is capable of pushing the test strip outward by the ejecting member, and thus users can remove the test strip from the holding device without drawing the test strip by hand, to eliminate the risk of infection. In addition, the sensing terminals of the bio-detecting instrument are not pressed or impacted by the holding device when ejecting the test strip outward, so as to prevent the sensing terminals from being deformed and affecting the test results.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
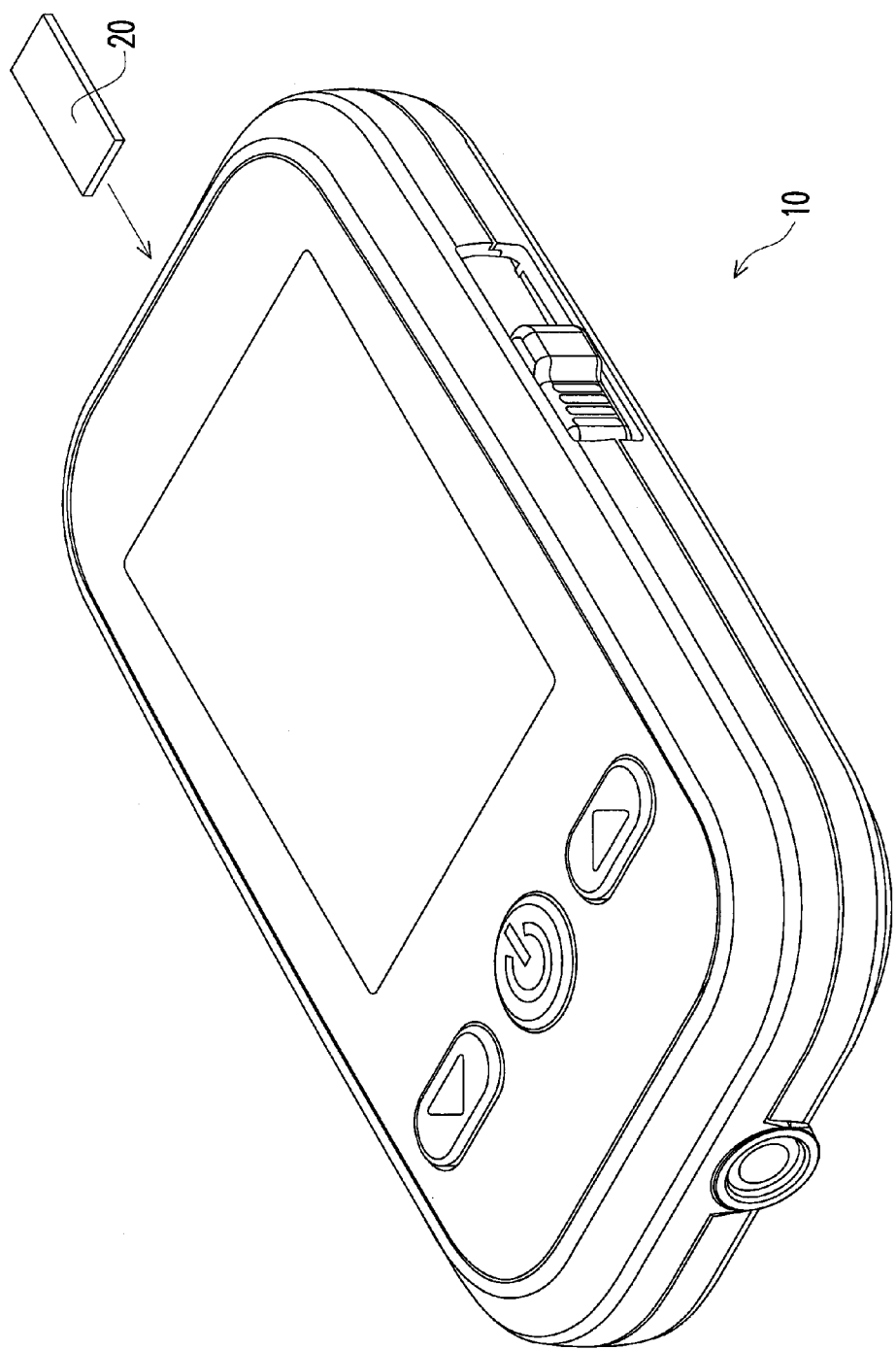
FIG. 1A is a perspective view of a bio-detecting instrument according to an embodiment of the present application.

Reference will now be made in detail to the present preferred embodiments of the invention, examples of which are illustrated in the accompanying drawings. Wherever possible, the same reference numbers are used in the drawings and the description to refer to the same or like parts.

Figure 1B:
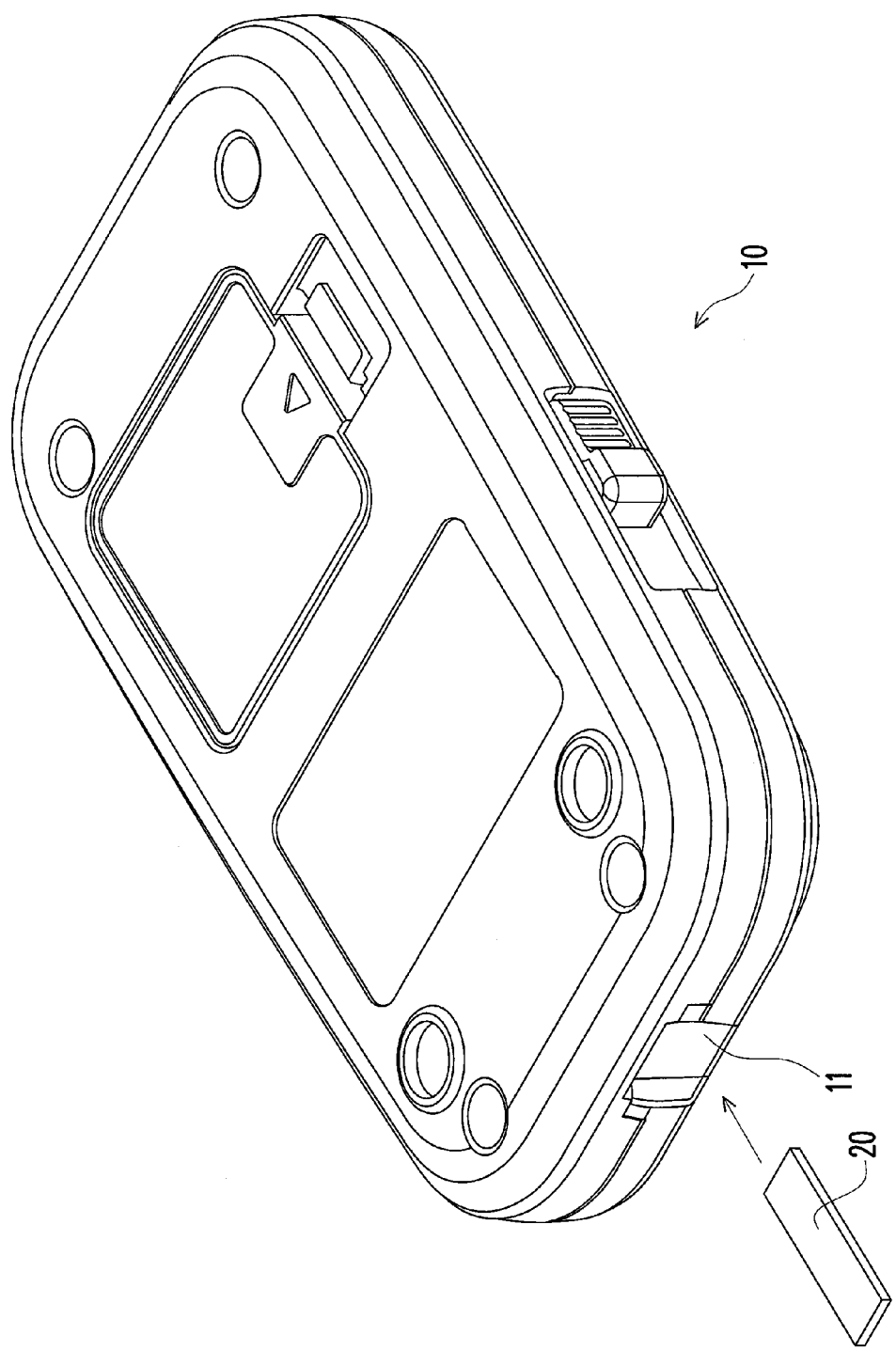
FIG. 1B is another perspective view of the bio-detecting instrument of FIG. 1A.

FIG. 1A is a perspective view of a bio-detecting instrument according to an embodiment of the present application. FIG. 1B is another perspective view of the bio-detecting instrument of FIG. 1A. Referring to FIG. 1A and FIG. 1B, the bio-detecting instrument 10 is provided with an opening 11, wherein a test strip 20 with test sample (e.g. blood sample) thereon is adapted to be inserted into the opening 11, and then test sample (e.g. blood sample) is provided on the test strip 20 for a biochemical test. The present embodiment provides a holding device 100 as shown in FIG. 2A through FIG. 2C, being adapted to be disposed in the bio-detecting instrument 10 for holding the test strip 20, and ejecting the test strip 20 outward after the biochemical test is completed, so as to remove the test strip 20 from the bio-detecting instrument 10 without drawing the test strip 20 by hand.

Figure 2A:
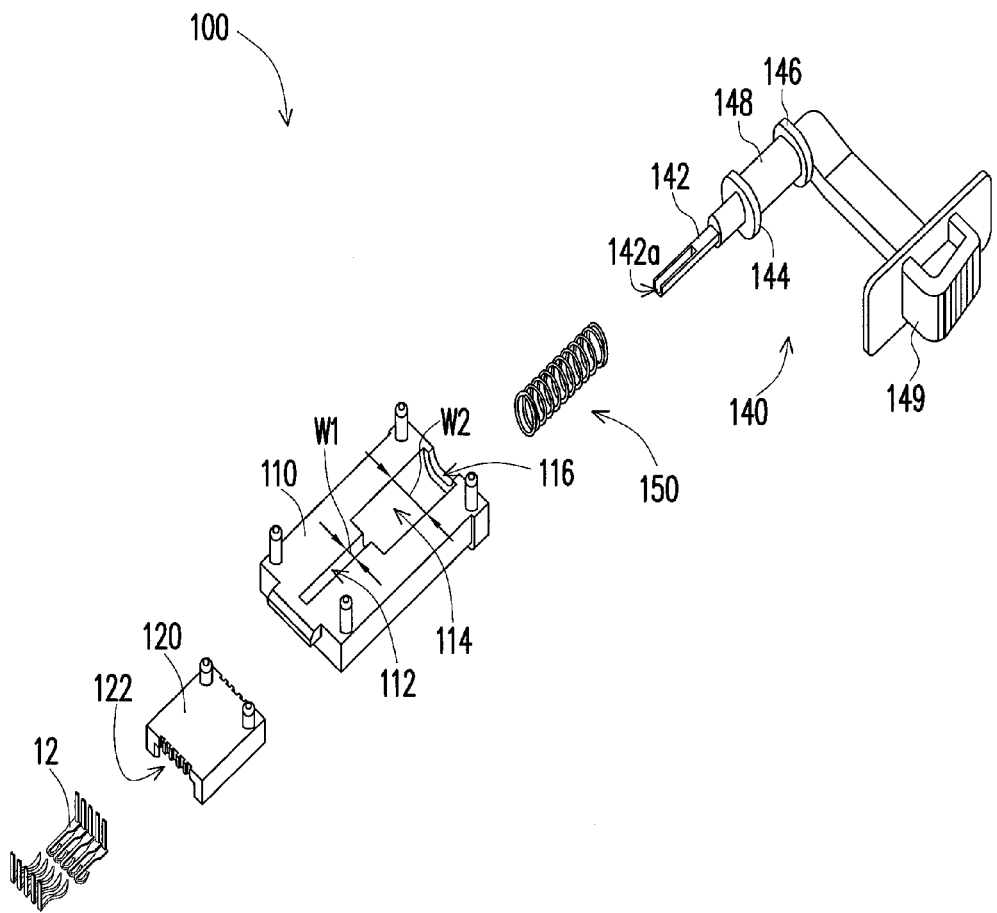
FIG. 2A is an explosive view of the holding device according to an embodiment of the present application.
Figure 2B:
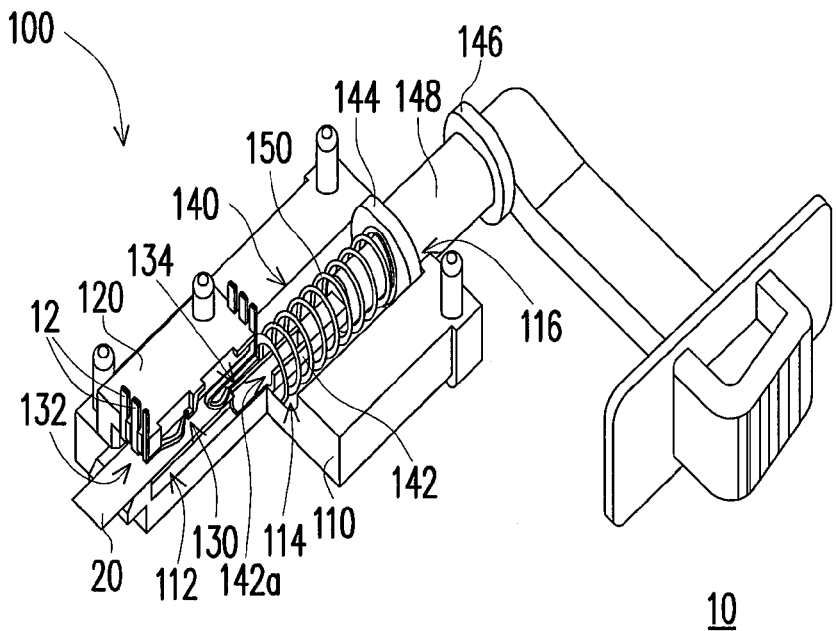
FIG. 2B is a perspective view of the holding device of FIG. 2A.
Figure 2C:
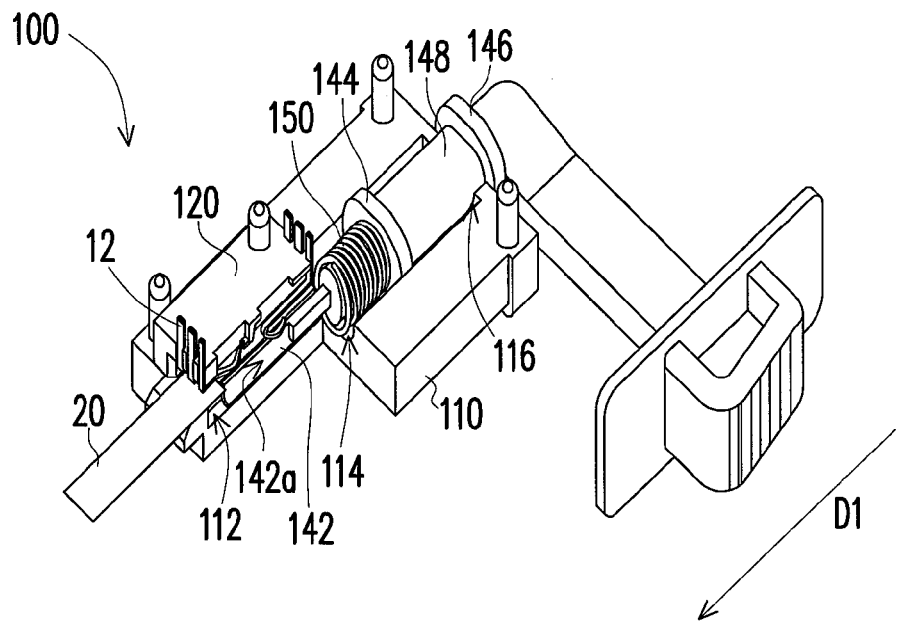
FIG. 2C illustrates an operating state of the holding device of FIG. 2B.

FIG. 2A is an explosive view illustrating the holding device 100, and FIG. 2B is a perspective view of the structure of FIG. 2A. Referring to FIG. 2A and FIG. 2B, the holding device 100 comprises a first casing 110, a second casing 120, an ejecting member 140, and an elastic member 150. The first casing 110 is provided with a first guiding groove 112, a second guiding groove 114, and a notch 116, wherein the second guiding groove 114 is connected to the first guiding groove 112, and the width W2 of the second guiding groove 114 is greater than the width W1 of the first guiding groove 112. The second casing 120 is provided with a cavity 122 for forming an accommodating space 130 by assembling the second casing 120 with the first casing 110, wherein the cavity 122 is connected between a first opening 132 and a second opening 134 of the accommodating space 130.

Sensing terminals 12 of the bio-detecting instrument 10 are extended into the accommodating space 130, wherein the sensing terminals 12 may be arranged in different heights, or be arranged horizontally, vertically, or the combination thereof. However, the arrangement of the sensing terminals 12 is not limited thereto, and depends on practical design requirements.

As a biochemical test is conducted, the test strip 20 thereon is inserted into the opening 11 of the bio-detecting instrument 10, and then the test strip 20 enters the accommodating space 130 through the first opening 132, and contacts the sensing terminals 12. The test sample provided on the test strip 20 can be detected by the bio-detecting instrument 10 through the sensing terminals 12.

The holding device 100 of the present embodiment is capable of ejecting the test strip 20 outward from the bio-detecting instrument 10 by the ejecting member 140. More specifically, the ejecting member 140 comprises a push rod 142, a first stopper 144, a second stopper 146, an intermediate connecting rod 148, and a handle portion 149. The push rod 142 is connected to the first stopper 144. The intermediate connecting rod 148 is connected between the first stopper 144 and the second stopper 146. The handle portion 149 is located at an end of the ejecting member 140. Particularly, the ejecting member 140 of the present embodiment is L-shaped, and the handle portion 149 is exposed from the bio-detecting instrument 10 (as shown in FIG. 1A and FIG. 1B). Therefore, a user can holding the bio-detecting instrument 10 and remove the test strip 20 by one hand. For example, the user can hold the bio-detecting instrument 10 by one hand and push the handle portion 149 exposed outside the bio-detecting instrument 10, to drive the push rod 142 and eject the test strip 20 outward from the bio-detecting instrument 10.

Furthermore, the ejecting member 140 of the present embodiment mat be integrally formed, such that the structure of the ejecting member 140 is steady, and the force applied on the handle portion 149 can be effectively transmitted to the push rod 142 and eject the test strip 20 outward.

Referring to FIG. 2B, the push rod 142 is configured to be reciprocated in the accommodating space 130 through the second opening 134. An outer profile of the push rod 142 of the present embodiment is matched with an inner profile of the first guiding groove 112. As shown in FIG. 2A, the first guiding groove 112 is semicircular, and the push rod 142 is a semi-cylinder, such that the push rod 142 can be reciprocated in the accommodating space 130 along the first guiding groove 112 by the conformity of profile between the first guiding groove 112 and the push rod 142, and the moving path and moving direction of the push rod 142 can be well defined by the first guiding groove 112. In addition, the push rod 142 is provided with a recessed portion 142a at a front end thereof.

In the present embodiment, a lateral profile of the first stopper 144 is matched with an inner profile of the second guiding groove 114, such that the first stopper 144 can slide along the second guiding groove 114. In addition, as shown in FIG. 2B, the first stopper 144 and the second stopper 146 are located at two opposite sides of the notch 116, wherein the notch 116 is arranged to restrict strokes of the first stopper 144 and the second stopper 146, and thereby the stroke of the ejecting member 140 is defined between an initial position and an ejecting position. The first stopper 144 and the second stopper 146 of the present embodiment are parallel with each other and have an identical profile.

Furthermore, the elastic member 150 is disposed between the second casing 120 and the first stopper 144 and disposed in the second guiding groove 114, so as to provide a resilience force to the ejecting member 140 for keeping or drawing the ejecting member 140 back to the position as shown in FIG. 2B. The elastic member 150 of the present embodiment is for example a spring surrounding the push rod 142. It is noted that the elastic member 150 is disposed in surrounding the push rod 142, such that the resultant moment on the ejecting member 140 caused by the resilience force can be reduced to approximately zero. Thus, the movement of the ejecting member 140 is more smooth and stable.

FIG. 2C illustrates an operating state of the holding device 100 of FIG. 2B wherein the biochemical test has been completed and the test strip 20 is removing from the bio-detecting instrument 10. Referring to FIG. 2C, the handle portion 149 of the ejecting member 140 is pushed along an ejecting direction D1 of the test strip 20, such that the ejecting member 140 moves from the initial position (as shown in FIG. 1B) to the ejecting position (as shown in FIG. 1C). The elastic member 150 is compressed by the first stopper 144 when the handle portion 149 is pushed along the ejecting direction D1, while the intermediate connecting rod 148 enters the second guiding groove 114, until the second stopper 146 is contact with and blocked by the notch 116. Meanwhile, the push rod 142 enters the accommodating space 130 and pushes the test strip 20 outward. It is noted that, the recessed portion 142a of the push rod 142 prevents the push rod 142 from being contact with the sensing terminals 12 as moving along the ejecting direction D1; more specifically, the recessed portion 142a of the push rod 142 is capable of accommodating the sensing terminals 12 when the push rod 142 enters the accommodating space 130. The sensing terminals 12 are protected by the recessed portion 142a without being contacted or deformed by the push rod 142. In other words, the sensing terminals 12 are protected from being affected or damaged by the ejecting member 140 by modifying the profile of the push rod 142.

Then, the force applied on the handle portion 149 is released after the test strip 20 is removed from the bio-detecting instrument 10, wherein the elastic member 150 becomes its initial length, the first stopper 144 returns to its original position, the push rod 142 leaves the accommodating space 130, and the ejecting member 140 goes back to the initial position as shown in FIG. 1B.

Figure 3:
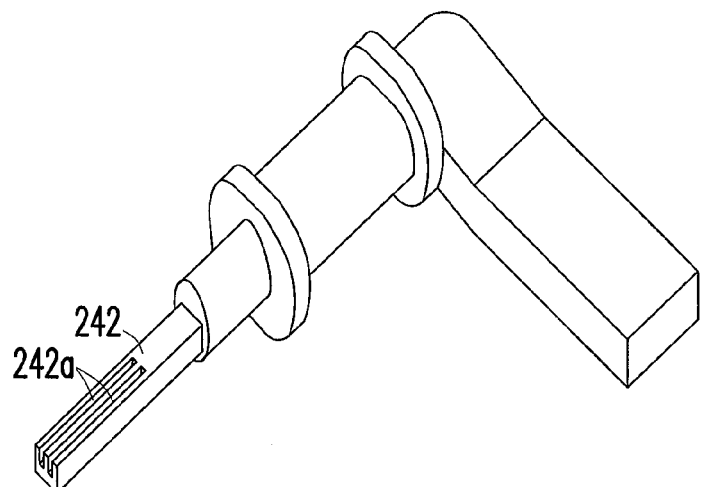
FIG. 3 through FIG. 5 illustrate various holding devices according to other embodiments of the present application, respectively.
Figure 4:
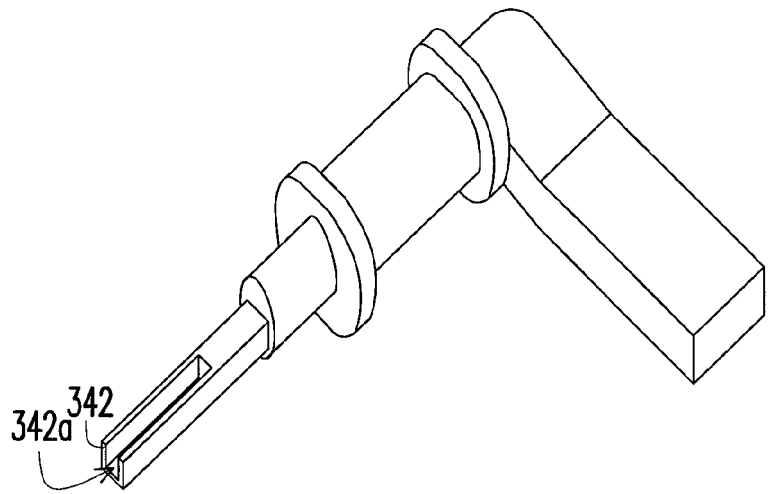
Figure 5:
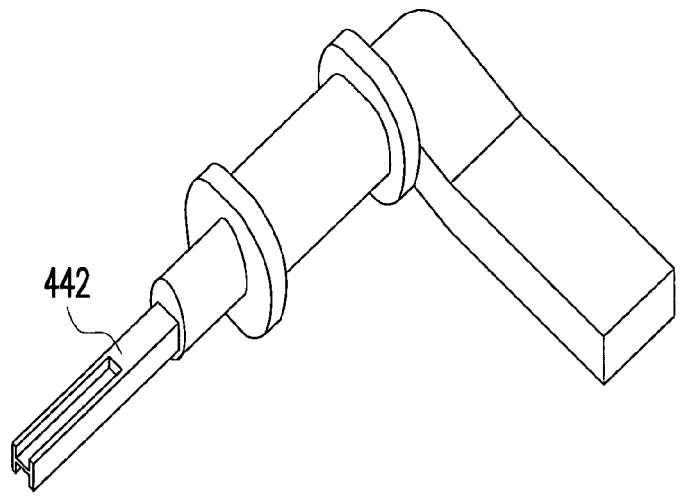

In the present embodiment, the front end of the push rod 142 is U-shaped to form the recessed portion 142a for accommodating the sensing terminals 12, so as to prevent the push rod 142 from continuously applying force to the sensing terminals 12 and deforming the sensing terminals 12. However, the front end of the push rod 142 can further be in other profiles. FIG. 3 through FIG. 5 illustrates various holding devices according to other embodiments of the present application, respectively. The front end of the push rod can further be in the profiles as shown in FIG. 3 through FIG. 5.

Referring to FIG. 3, the front end of the push rod 242 has two recessed portions 242a, wherein the amount and position of the recessed portions 242a are corresponding to those of the recessed portion 242a, such that the recessed portions 242a can accommodate the sensing terminals 12 and protect the sensing terminals 12 from being deformed when the push rod 242 enters the accommodating space 130 (as shown in FIG. 2C). In addition, the profile of the recessed portion may be corresponding to that of the first guiding groove, for example, as shown in FIG. 4, the recessed portion 342a at the front end of the push rod 342 is rectangular angled as well as the first guiding groove 112 in FIG. 2A. Referring to FIG. 5, the front end of the push rod 442 is H-shaped, and correspondingly, the sensing terminals 12 (as shown in FIG. 2A through FIG. 2C) can be disposed at the upper side or lower side of the push rod 442, or be disposed at both sides of the push rod 442. In further another embodiment, a flat push rod without any recessed portion may be provided. However, the profile of the push rod of the present application is not limited to the aforementioned embodiments, as long as the push rod can push the test strip 20 outward from the accommodating space 130 without excessively compressing or deforming the sensing terminals 12.

In summary, the holding device of the present application can remove a test strip by ejecting member without drawing the test strip by hand, so as to eliminate the risk of infection. In addition, sensing terminals of the bio-detecting instrument are not pressed or impacted by the holding device when ejecting the test strip outward, so as to prevent the sensing terminals from being deformed and affecting the test results.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A holding device, disposed in a bio-detecting instrument having a plurality of sensing terminals, for holding a test strip, the holding device comprising:
    a first casing;
    a second casing, assembled with the first casing to form an accommodating space there between, wherein the sensing terminals are extended into the accommodating space, and the test strip is configured to be delivered into the accommodating space through a first opening and contact with the sensing terminals;
    an ejecting member, comprising a push rod, a first stopper connected to the push rod, a second stopper, an intermediate connecting rod located between the first stopper and the second stopper and a handle portion connected to the second stopper, wherein the push rod is configured to be reciprocated in the accommodating space through a second opening, the handle portion is extended to outside of the bio-detecting instrument, and the ejecting member is integrally formed; and
    an elastic member, disposed between the second casing and the first stopper, wherein
    the elastic member is configured to be compressed by driving the ejecting member to an ejecting position, where the push rod enters the accommodating space and is adapted to push the test strip outward without being contact with the sensing terminals, and the elastic member is configured to be released by drawing the push rod back from the accommodating space to an initial position, and the elastic member is disposed in surrounding the push rod, wherein the first casing is provided with a notch for restricting strokes of the first stopper and the second stopper, the first stopper and the second stopper are respectively located at two opposite sides of the notch, and a connection line of the first stopper and the second stopper passes through the notch.

2. The holding device of claim 1, wherein the first casing is provided with a first guiding groove having an inner profile matched with an outer profile of the push rod, so as to guide the push rod sliding in the accommodating space.

3. The holding device of claim 2, wherein the first casing is provided with further a second guiding groove connected to the first guiding groove, and the first stopper is configured to slide along the second guiding groove.

4. The holding device of claim 3, wherein the intermediate connecting rod is located in the second guiding groove when the ejecting member is driven to the ejecting position.

5. The holding device of claim 4, wherein the first stopper and the second stopper are parallel with each other.

6. The holding device of claim 3, wherein the elastic member is located in the second guiding groove.

7. The holding device of claim 1, wherein the push rod is provided with a recessed portion, and the sensing terminals are configured to pass through the recessed portion when the ejecting member is reciprocated between the initial position and the ejecting position.

8. The holding device of claim 1, wherein the second casing is provided with a cavity for forming the accommodating space by assembling the second casing with the first casing, and the cavity is connected between the first opening and the second opening of the accommodating space.

* * * * *